United States Patent
Avitall (10) Patent No.: US 10,492,858 B2
(45) Date of Patent: Dec. 3, 2019

(54) ASSESSMENT OF TISSUE CONTACT IN TISSUE ABLATION

(71) Applicant: Boaz Avitall, Milwaukee, WI (US)

(72) Inventor: Boaz Avitall, Milwaukee, WI (US)

( * ) Notice: Subject to any disclaimer, the term of this patent is extended or adjusted under 35 U.S.C. 154(b) by 391 days.

(21) Appl. No.: 15/411,323

(22) Filed: Jan. 20, 2017

(65) Prior Publication Data

US 2017/0209203 A1 Jul. 27, 2017

Related U.S. Application Data (60) Provisional application No. 62/281,414, filed on Jan. 21, 2016.

(51) Int. Cl.
| | |
|---|---|
| *A61B 18/12* | (2006.01) |
| *A61B 18/14* | (2006.01) |
| *A61B 18/00* | (2006.01) |

(52) U.S. Cl.
CPC ............. *A61B 18/1492* (2013.01); *A61B 2018/00029* (2013.01); *A61B 2018/00577* (2013.01); *A61B 2018/00642* (2013.01); *A61B 2018/00744* (2013.01); *A61B 2018/00791* (2013.01); *A61B 2218/002* (2013.01)

(58) Field of Classification Search
CPC .......... A61B 18/14; A61B 2018/00577; A61B 2018/00791
See application file for complete search history.

(56) References Cited

U.S. PATENT DOCUMENTS

| | | | |
|---|---|---|---|
| 6,063,078 A * | 5/2000 | Wittkampf | A61B 18/1492 606/41 |
| 6,761,716 B2 | 7/2004 | Kadhiresan et al. | |
| 2005/0004513 A1* | 1/2005 | Beyerlein | A61B 5/03 604/66 |
| 2005/0096644 A1* | 5/2005 | Hall | A61B 18/14 606/41 |
| 2006/0259023 A1* | 11/2006 | Abboud | A61B 5/053 606/21 |
| 2011/0152857 A1 | 6/2011 | Ingle | |
| 2011/0224573 A1* | 9/2011 | Bar-Tal | A61B 18/1492 600/549 |
| 2012/0239019 A1* | 9/2012 | Asconeguy | A61B 18/1492 606/33 |

FOREIGN PATENT DOCUMENTS

WO  WO200122895  4/2001

* cited by examiner

*Primary Examiner* — Daniel W Fowler
(74) *Attorney, Agent, or Firm* — Dewitt LLP; Thomas J. Nikolai (57) ABSTRACT

A device and method for determining ablation electrode to tissue contact to assess the effectiveness of an ablation procedure by determining the effect of saline irrigation on catheter tip temperature.

4 Claims, 8 Drawing Sheets

ASSESSMENT OF TISSUE CONTACT IN TISSUE ABLATION

CROSS-REFERENCE TO RELATED APPLICATIONS

This application is a non-provisional application of Application No. 62/281,414, filed Jan. 21, 2016 and claims priority from that application which is also deemed incorporated by reference in its entirety in this application.

STATEMENT REGARDING FEDERALLY SPONSORED RESEARCH OR DEVELOPMENT

Not applicable.

BACKGROUND OF THE INVENTION

I. Field of the Invention

The present invention relates generally to the field of catheter-based RF tissue ablation devices and techniques and, more particularly, to catheter devices and methods for assessing the efficiency of electrode-tissue contact related to the effectiveness of tissue ablation to relieve atrial cardiac arrhythmias. Specifically, the invention provides a device and method for determining ablation electrode to tissue contact before and during an ablation procedure and the estimation of tissue heating during RF application.

II. Related Art

Cardiac arrhythmias, particularly atrial fibrillation, are common and dangerous medical conditions causing abnormal, erratic cardiac function. Atrial fibrillation is observed particularly in elderly patients and results from abnormal conduction and automaticity in regions of cardiac tissue. Chronic atrial fibrillation (AF) may lead to serious conditions including stroke, heart failure, fatigue and palpitations. The treatment of chronic AF requires the creation of a number of transmural contiguous linear lesions. The use of a pattern of surgical incisions and thus surgical scars to block abnormal electrical circuits, and passageways known as the Cox Maze procedure, has become the standard surgical procedure for effective surgical cure of AF. The procedure requires a series of full-thickness incisions to isolate the pulmonary veins and the posterior wall of the left atria. Additional lines involve the creation of lesions from the posterior wall to the mitral valve, at the atrial isthmus line and superior vena cava (SVC) to the inferior vena cava (IVC) with a connection to the right atrial appendage.

Catheters have been developed that make the corrective procedure less invasive. They are designed to create lesions by ablation of tissue that perform the function of the surgical incisions. These include catheters that attempt to connect a series of local or spot lesions made using single electrodes into linear lesions. Devices that use a linear array of spaced electrodes or electrodes that extend along the length of a catheter have also been used.

Important drawbacks found fundamental in the current catheter-based ablation approaches can be attributed to several factors including a lack of consistent contact between the ablation devices and the target tissues, and the inability to accurately determine the degree of ablation electrode contact with the targeted tissue prior to and during the ablation procedure.

Effective RF tissue ablation is a function of the ablation electrode contact with the targeted tissue and the current density that result in tissue heating and tissue destruction. The most effective lesion is created if the ablation electrode is imbedded in the tissue. Clearly, the assumption that the application of increasing force increases the tissue surface contact with the ablation tip resulting in an effective lesion. However, in a thick, stiff tissue, such as the AV junction, increasing force may translate to only a small improvement in contact area, whereas in thin pliable tissues, such as the PV/LA junction, the same contact force results in the catheter creating a pouch that is likely to lead to extra-cardiac injuries and possible cardiac perforation. Several technologies are currently in clinical use measuring the ablation catheter contact force. These technologies utilizing laser and electromagnetic sensors do not provide any information regarding the ablation electrode to tissue contact and also are costly. Another approach that is also used is an algorithm assessment of contact based on impedance change associated with the impedance differences of blood vs. tissue.

Additional limitation of the current ablation technologies is the lack of information regarding the tissue temperature. To avoid char formation from overheating the tissue that can lead to stroke most if not all ablation procedures applied in the left atria employ open irrigated catheters. The irrigation flow cools the ablation electrode and removes/dilutes the blood trapped between the electrode and the tissues preventing char formation during the RF application. As a result of the cooling by the irrigation the temperature measurement of RF tissue heating is not possible. The proposed technology will allow not only assessment of the catheter-to-tissue contact but also an assessment of tissue heating during the RF application.

SUMMARY OF THE INVENTION

The current disclosure capitalizes on using saline irrigation and embedded temperature sensors to define the extent of contact based on a temperature profile and/or the pressure of saline flow.

One embodiment uses fixed volume pulses of relatively cold saline. If the catheter is floating in the cardiac chamber and not imbedded, a pulse injection of saline at a temperature, for example, of ~2° C. will minimally affect the catheter temperature sensors with no increase in resistance to flow above baseline. In contrast, if the catheter is totally embedded in the tissues, the injection of ~2° C. cold saline will bathe the catheter tip and prolong rewarming from the surrounding tissues and blood flow creating a unique temperature profile. In addition, the resistance to flow of the injection will be incrementally higher, as well.

A second aspect of this application is associated with the estimation of tissue heating based on the post ~2° C. pulse injection during RF ablation application. In a similar profile of temperature change, the injection of a fixed volume over a fixed time period, such as 2 seconds during RF application, will result in a temperature change recorded by the catheter temperature sensors that will be tempered by heat load emanating from tissues. Whereas the blood is at a constant temperature, the tissues are heated by RF current to levels of 50-80 and at times even >100 degrees above the circulating blood temperature.

The higher the tissue temperature, with an embedded ablation tip after the injection of cold saline, the faster it will rewarm vs. pre-ablation cold saline injection. A pre-ablation cold (~2° C.) saline injection is used to establish a reference profile. Tissue overheating that can lead to boiling will rapidly overcome the cold saline injection whereas low tissue heating will result in prolong temperature recovery. These measurements need to be done under fixed power control.

Catheter tissue contact information can also be derived using pulses of ambient or room temperature saline irrigation at a 2 cc/min at about 20° C.-24° C. The temperature profile of a plurality of temperature sensors is an indication of the tip to tissue contact. It has been found that an irrigated RF catheter will undergo a significantly greater temperature reduction when the catheter is in good contact with tissues particularly in the distal region of the catheter tip. Minimal or no temperature change will occur in poor contact or floating catheter situations.

Several Technology Requirements Need to be Considered:
1) The ablation tip needs to be constructed from highly conductive metal;
2) The temperature sensors need to be close to the outer surface of the ablation tip;
3) The temperature measurement sensors need to be high fidelity rapid response, preferably, several sensors are placed around the ablation tip;
4) Irrigation ports need to be evenly distributed and it has been found that, generally, there should be a plurality of small irrigation ports, as many as 16 or more, preferably.

DETAILED DESCRIPTION

The following description is meant to illustrate the concepts of the present invention without limiting the scope thereof.

Figure 1A:
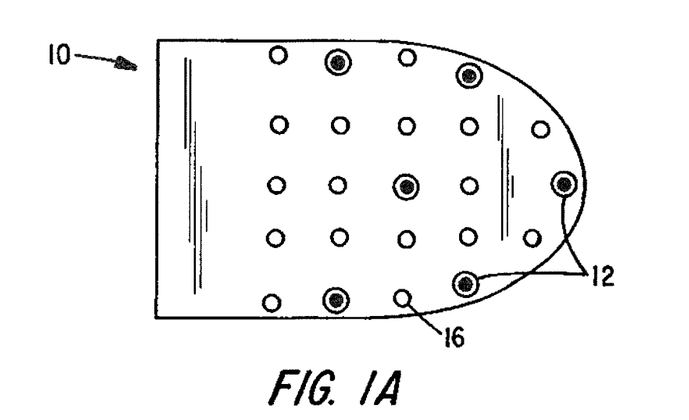
FIGS. 1A-1C are enlarged two dimensional images of ablation catheter tip areas showing temperature sensors and irrigation ports in accordance with the invention.

In one embodiment, it has been found that an irrigated ablation catheter equipped with a plurality of temperature sensors placed at the surface and insulated from the ablation electrodes is one embodiment that can be used to evaluate tissue contact in accordance with the invention. Such a catheter tip is shown in FIG. 1A with tip 10 and sensors 12. Irrigation is accomplished using saline solution administered from multiple irrigation ports in the catheter tip as an injected pulse of fixed volume.

Figure 1B:
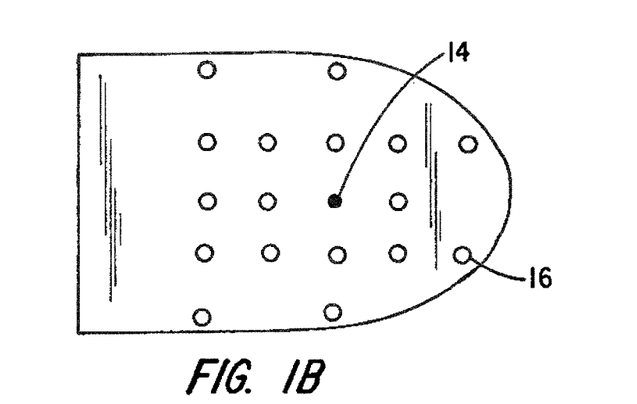
Figure 1C:
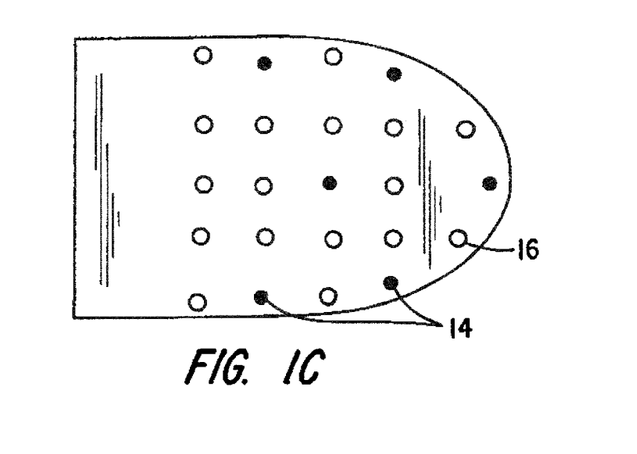
Figure 2A:
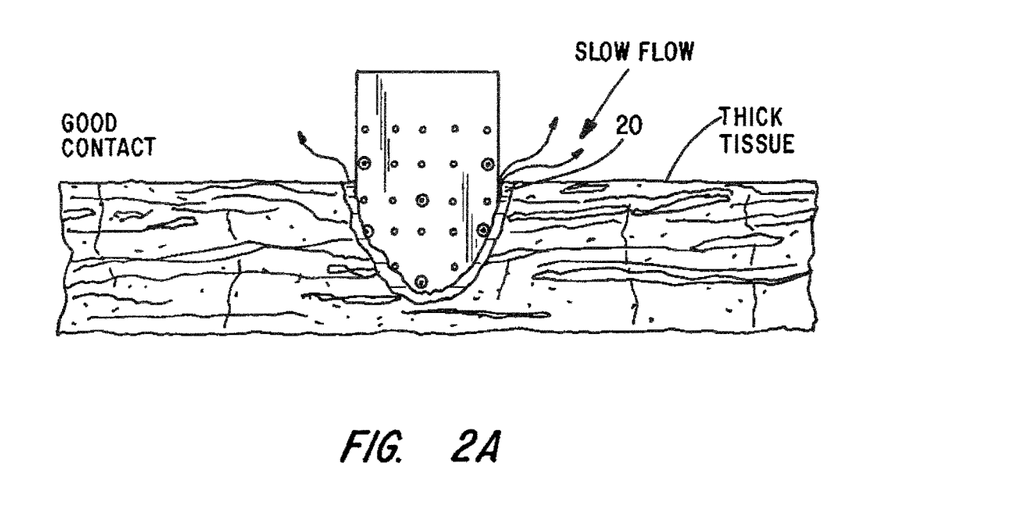
FIGS. 2A and 2B illustrate good or effective contact between an ablation catheter tip and relatively thick tissues.
Figure 2B:
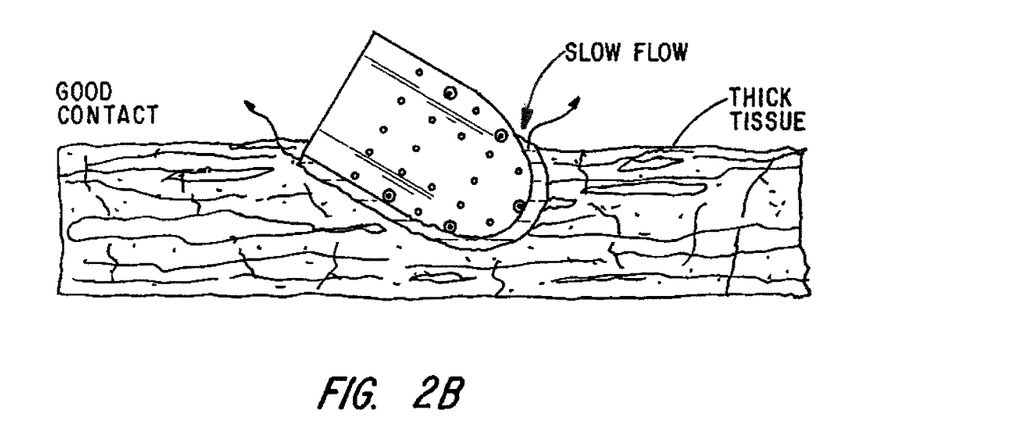
Figure 3A:
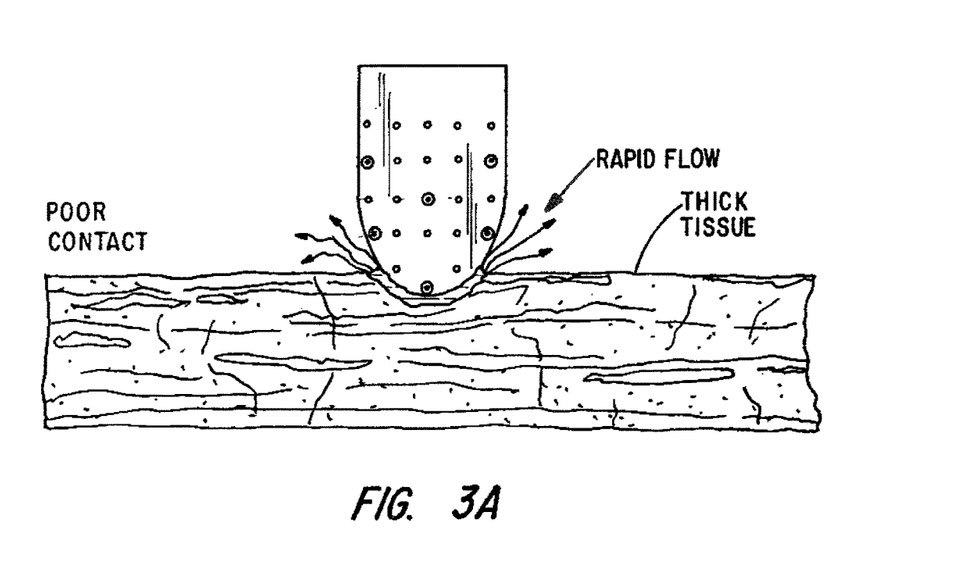
FIGS. 3A and 3B illustrate less effective or poor contact between an ablation catheter tip and thick tissue.
Figure 3B:
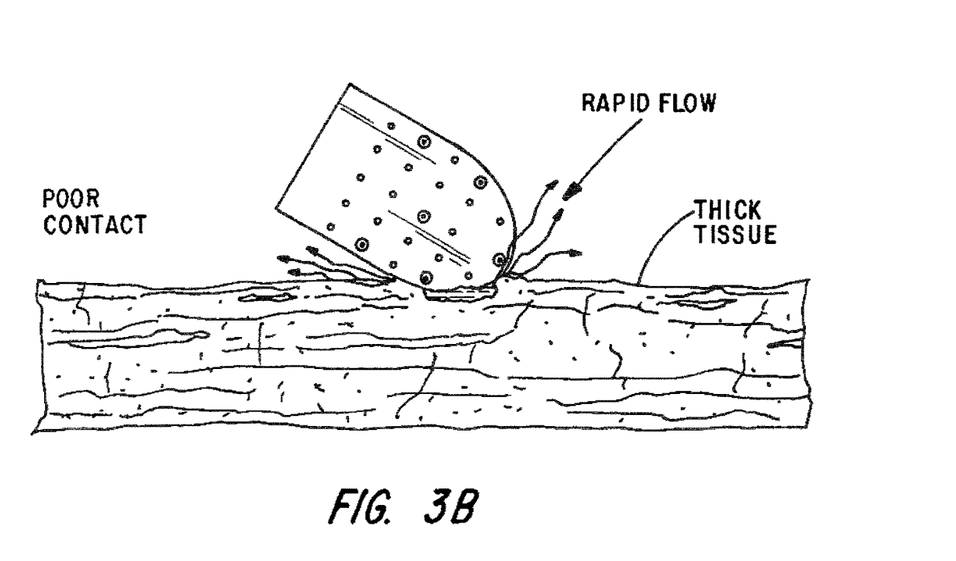
Figure 4A:
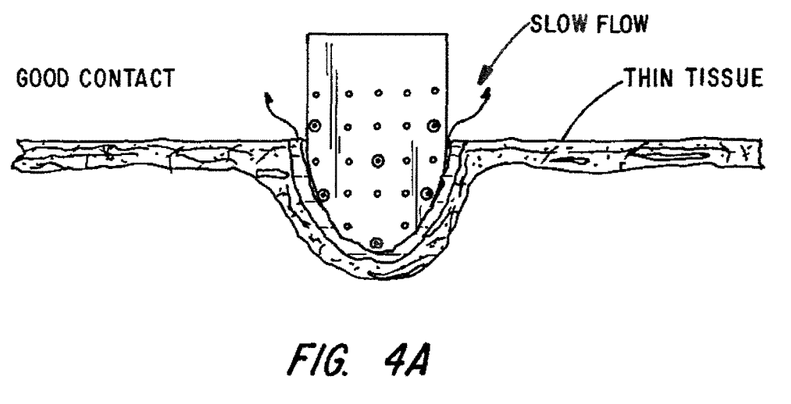
FIGS. 4A and 4B illustrate good or effective contact between an ablation catheter tip and relatively thin tissue.
Figure 4B:
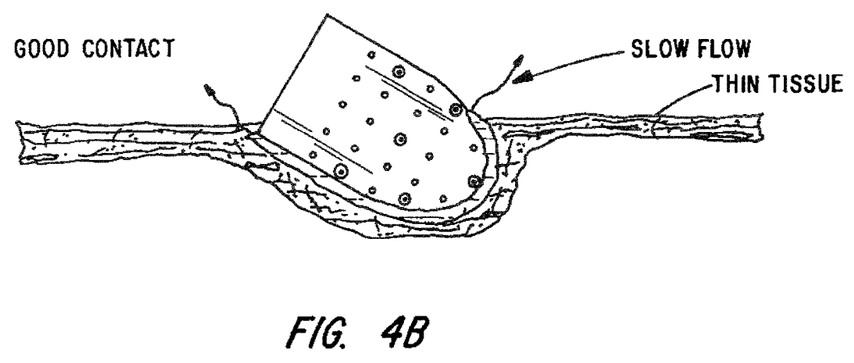
Figure 5A:
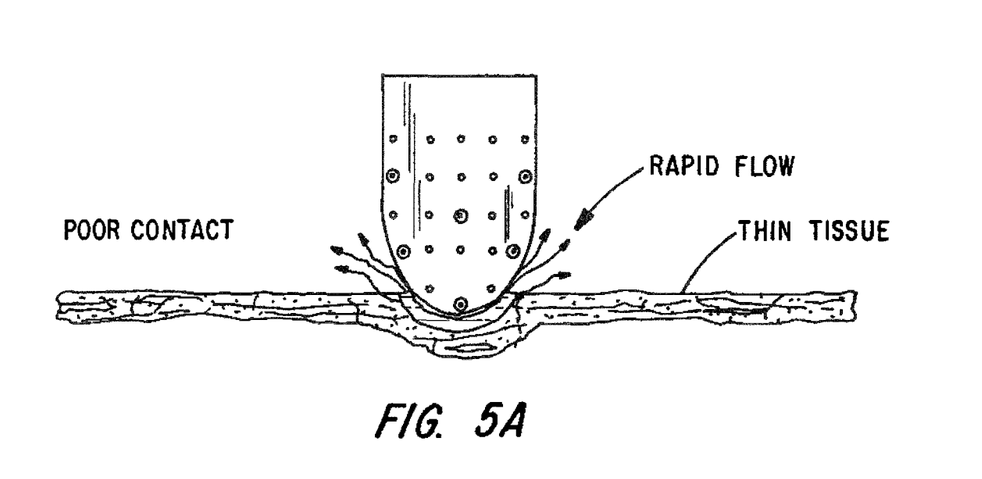
FIGS. 5A and 5B illustrate less effective or poor contact between an ablation catheter tip and relatively thin tissue.
Figure 5B:
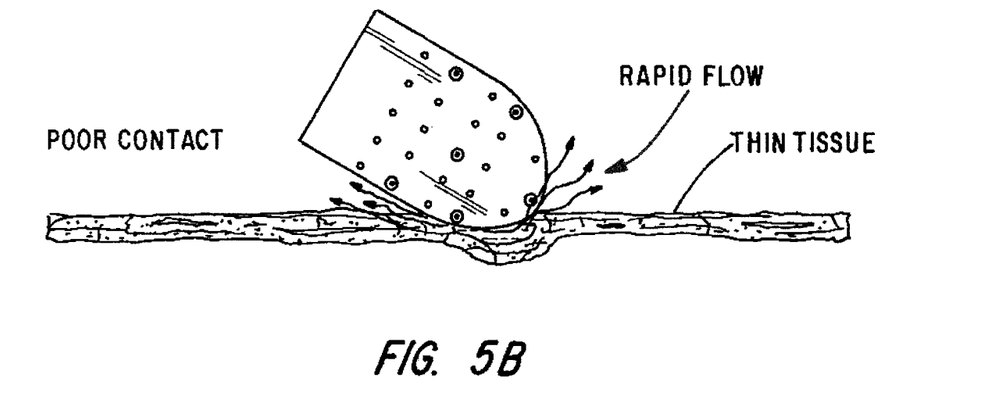

In other embodiments, a plurality of temperature sensors may be placed below the outer surface of the ablation catheter, as shown at 14 in FIG. 1C, or a single temperature sensor 14 may be placed at the center of the ablation electrode of interest as shown in FIG. 1B. Irrigation ports are shown at 16.

Figure 6:
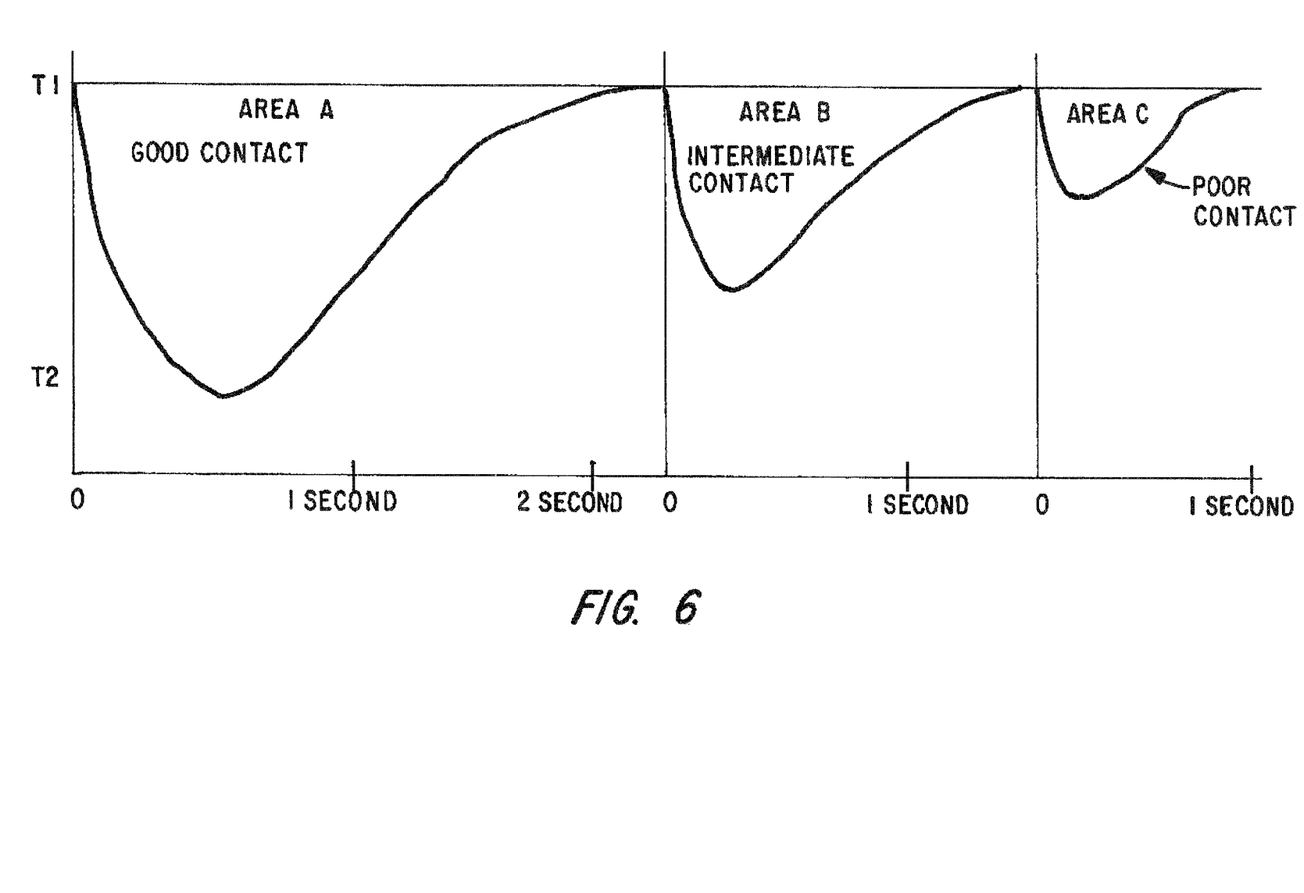
FIG. 6 illustrates an estimation of three temperature profiles based on temperature dip and recovery reacting to a saline injection at the site of tissue contact as a measure of contact level.
Figure 7:
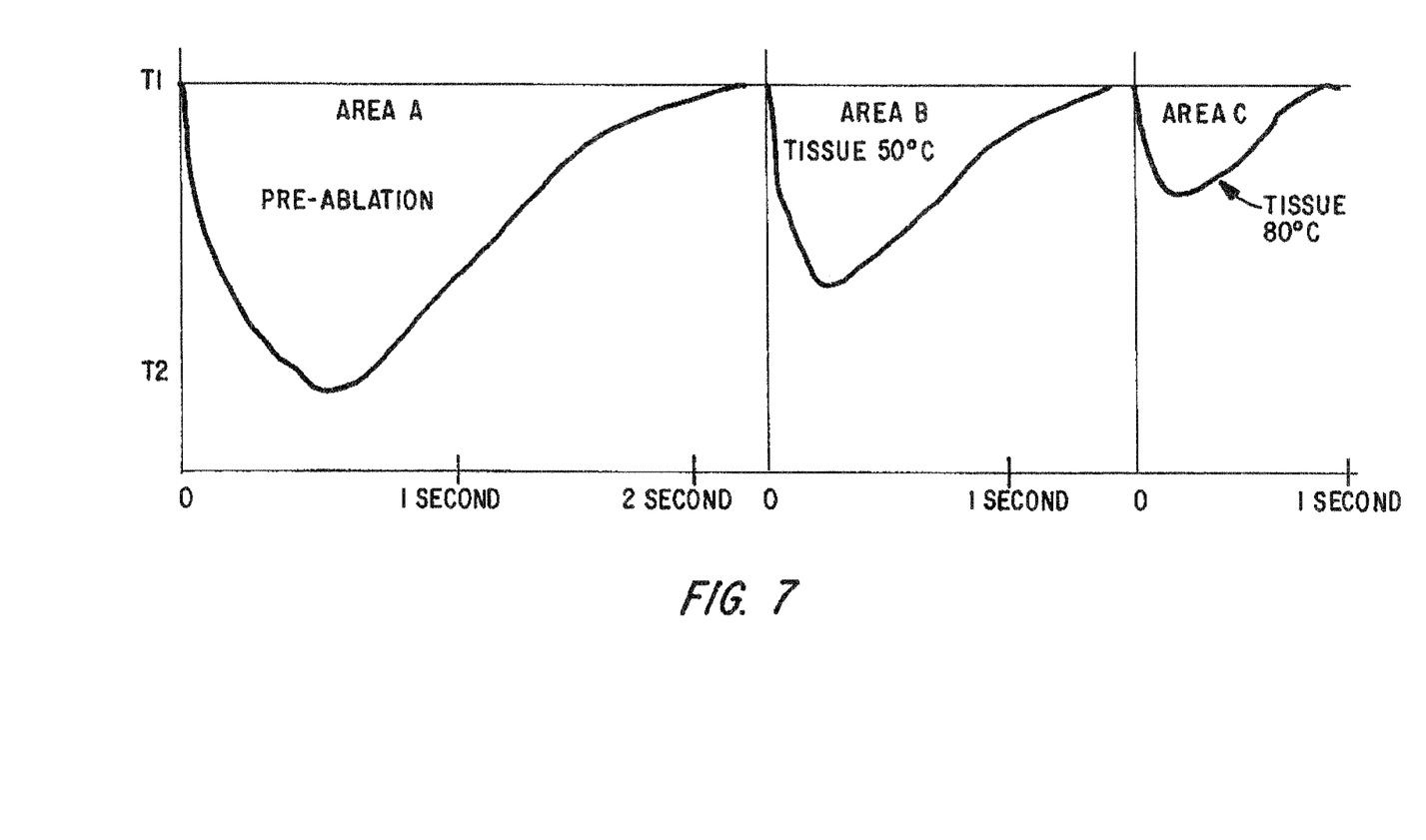
FIG. 7 is a figure similar to FIG. 6 with the temperature profiles further used to define tissue temperature before and during ablation.

Each of the embodiments can be used to map a pressure (optional) or temperature profile after a pulsed saline injection using a fixed dose and rate. Integration of the area associated with the curve has been found to be directly related to the contact level. Algorithms are being developed to determine actual catheter to tissue contact values based on the temperature or pressure profile and to determine tissue heating during RF ablation based on the temperature profile associated with the injection of cold saline, a fixed dose, rate and intervals. As seen in FIGS. 6 and 7, the hotter the tissue, the faster and smaller the temperature change, with a cold saline injection and, thus, a smaller area associated with the curve. The heat load within the tissue is related to the area of contact (determined prior to the initiation of RF) and during the application of the RF power. The curve is based on pre-ablation treatment, as in area A of FIG. 7. The area under curve B is associated with a tissue temperature plotted during 10 sec. of CF ablation when recovery is faster. Curve B may relate to a tissue temperature of about 50° C. Curve C represents an even hotter tissue temperature of perhaps 80° C.

As shown in FIGS. 2A-5B, the cooled saline 20 accumulates under the catheter with when the catheter is in good contact whereas in poor contact the cooled saline rapidly dissipates into the blood circulation.

The preferred ablation catheter has many irrigation ports at or near the catheter tip and a plurality of temperature sensors around the catheter placed very close to the surface or at the surface of the tip area. The RF ablation tip should be highly conductive to transmit temperature accurately.

Temperature drops at high irrigation rates also appear to be indicative of contact quality. Table I summarizes, over N=5 tests, the average distal temperature drop measured with an irrigation flow rate of 15 ml/min and a temperature monitoring period of 5 s. It shows that higher contact force values (in grams) result in larger temperature drops.

TABLE I

| Force (g) | Distal temp drop (C.) |
| --- | --- |
| 0gr_ABL.txt | −2.0 |
| 1gr_ABL.txt | −2.3 |
| 5gr_ABL.txt | −3.0 |
| 10gr_ABL.txt | −3.3 |
| 15gr_ABL.txt | −3.6 |
| 20gr_ABL.txt | −3.5 |
| 30gr_ABL.txt | −3.8 |
| 40gr_ABL.txt | −4.3 |

Figure 8:
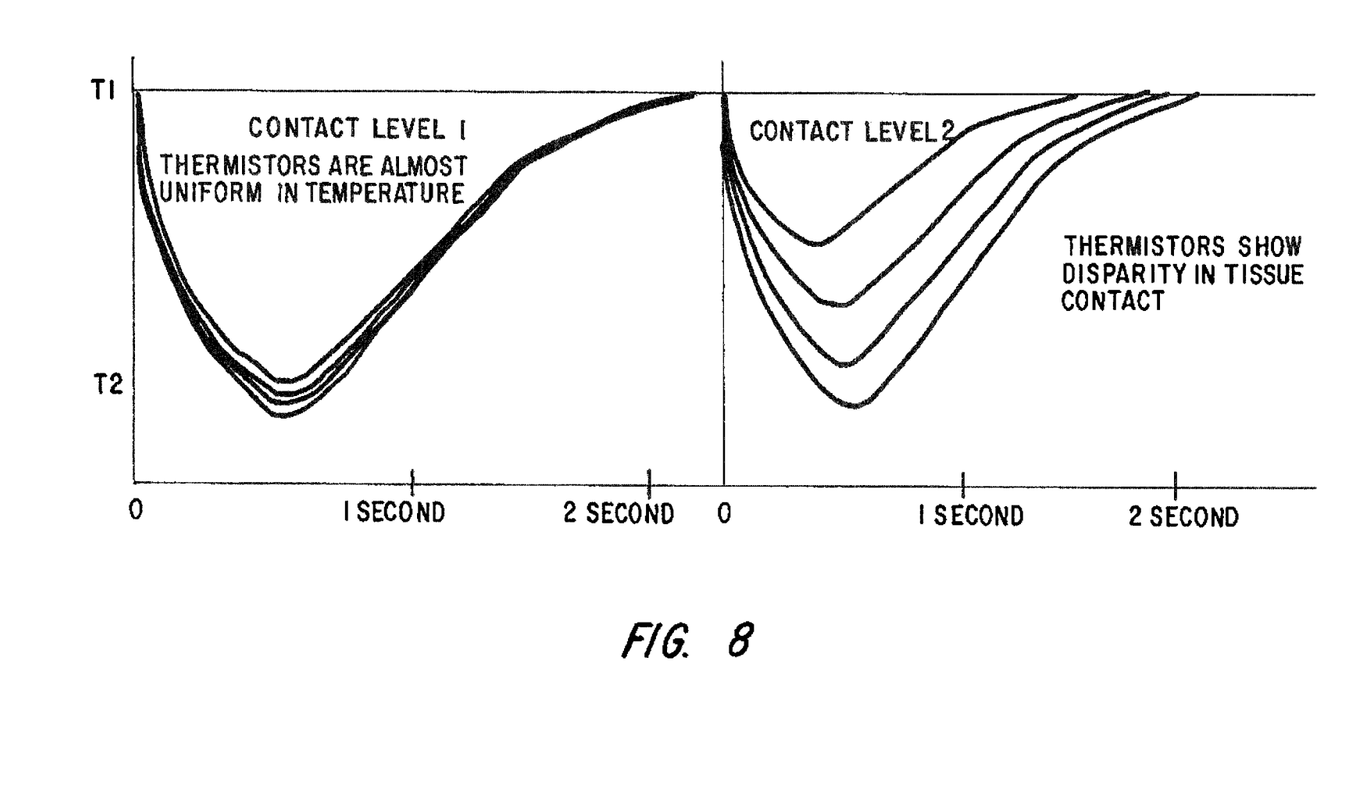
FIG. 8 shows further profiles representing catheter to tissue contact for post 3 cc 2° C. cold saline injection dip and recovery profile.

FIG. 8 shows catheter-to-tissue contact based on post 3 cc 1 sec. cold saline injection temperature drop and recovery profile based on a catheter tip having four thermocouple temperature sensors related to the ablation electrode. The uppermost curve represents the most proximal temperature sensor and the lowest curve represents the most distal temperature sensor. Contact level 1 represents a reaction based on good catheter-to-tissue contact and contact level 2 represents poor catheter-to-tissue contact. In contact level 1, the temperature of the thermocouple or thermistor temperature sensors uniformly drop to a low level and recovery is relatively slow and uniform as well. In contact level 2, where the catheter is just touching the tissue, one temperature sensor (bottom) shows good tissue contact and the others show significantly less and less contact with lower reduction in temperature and more rapid temperature recovery.

EXAMPLE I

An irrigated RF catheter with 6 temperature sensors positioned circumferentially distally and proximally on the surface of the ablation tip was used to test the hypothesis that irrigation at 2 cc/min with room temperature saline (20° C.) will result in significantly lower baseline temperatures when the ablation tip is in contact with tissues. Conversely, minimal or no temperature change will occur when the catheter ablation tip is in poor or no contact with tissues.

Objective: Utilize an inexpensive, non-invasive and simple technology to reliably determine tissue contact.

Methods: In 5 animals 85 RF lesions were placed in well-defined identifiable anatomical locations guided by 3D navigation in both atria and ventricles. The catheter contact variability was adjusted to good, fair, and poor based on pace threshold, local electrogram amplitude (EGM), and confirmed by the maximal impedance reduction during ablation and lesion width, length and depth.

Results: As shown in Table II, significant and distinct temperature differentiation is noted between good, fair, and poor contact. This is confirmed by the significant differences in pre/post pace threshold, EGM amplitude, impedance drop during RF application, and finally, lesion size.

Conclusion: Surface mounted temperature sensors on an irrigation catheter allows for distinct differentiation of catheter to tissue contact levels at 2 cc of irrigation and may eliminate the need for expensive complicated force contact technology.

TABLE II

| Contact Assessment | Temp Reduction | | Lesion Dimensions (mm) | | | Impedance Decrease |
| --- | --- | --- | --- | --- | --- | --- |
| Contact Level | Distal | Proximal | Length | Width | Depth | Ohms |
| Good | −6.2 ± 0.8¶*, †* | −4.2 ± 1.7¶*, †* | 7.4 ± 3.9¶$^{NS}$, †* | 7.5 ± 4.0¶$^{NS}$, †* | 2.7 ± 2.4¶$^{NS}$,†* | 30 ± 9¶*, †* |
| Fair | −4.6 ± 0.2‡* | −2.5 ± 0.6‡* | 6.9 ± 4.4‡* | 6.8 ± 3.4‡* | 2.7 ± 2.4‡* | 28 ± 11‡* |
| Poor | −2.8 ± 1.4 | −1.3 ± 1.1 | 2.4 ± 3.1 | 2.9 ± 3.7 | 0.3 ± 0.4 | 9 ± 4 |

¶= Good versus Fair,

†= Good versus Poor,

‡= Fair versus Poor,

Significance M

This invention has been described herein in considerable detail in order to comply with the patent statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

What is claimed is:

1. A method of determining the state of electrode to tissue contact in a catheter-based tissue ablation device comprising:
    a) providing an irrigated ablation catheter with a metal ablation tip having a plurality of temperature measurement sensors distributed about the metal ablation tip and a plurality of irrigation ports distributed about the metal ablation tip and at least one ablation electrode on the metal ablation tip insulated from said temperature measurement sensors;
    b) with the metal ablation tip in contact with tissue to be ablated, applying irrigation pulses of 1-3 cc of saline solution at a predetermined temperature and flow rate through said irrigation ports and measuring the resulting distal and proximal ablation tip temperature profile of the irrigated metal ablation tip.

2. A method as in claim 1 wherein the amount of temperature reduction in the metal ablation tip caused by the saline is a measure of the tissue contact effectiveness.

3. A method as in claim 1 including measuring the metal ablation tip pressure when said irrigation pulses are being applied.

4. A method of determining the state of electrode to tissue contact in a catheter-based tissue ablation device comprising:
    a) providing an irrigated ablation catheter with a metal ablation tip having a plurality of temperature measurement sensors distributed about the metal ablation tip and a plurality of irrigation ports distributed about the metal ablation tip and at least one ablation electrode on the metal ablation tip insulated from said temperature measurement sensors;
    b) with the metal ablation tip in contact with tissue to be ablated, applying irrigation pulses of saline solution at a predetermined flow rate and temperature through said irrigation ports and measuring the resulting temperature profile of the irrigated metal ablation tip wherein the rate of temperature decrease and recovery is used as an indication of tissue contact effectiveness.

* * * * *